(12) United States Patent
Hosogi

(10) Patent No.: US 10,014,156 B2
(45) Date of Patent: Jul. 3, 2018

(54) CALIBRATION METHOD AND CHARGED PARTICLE BEAM SYSTEM

(71) Applicant: JEOL Ltd., Tokyo (JP)

(72) Inventor: Naoki Hosogi, Tokyo (JP)

(73) Assignee: JEOL Ltd. (JP)

( * ) Notice: Subject to any disclaimer, the term of this patent is extended or adjusted under 35 U.S.C. 154(b) by 0 days.

(21) Appl. No.: 15/331,033

(22) Filed: Oct. 21, 2016

(65) Prior Publication Data

US 2017/0117116 A1    Apr. 27, 2017

(30) Foreign Application Priority Data

Oct. 23, 2015 (JP) .................................. 2015-208771

(51) Int. Cl.
*H01J 37/20* (2006.01)
*G01B 15/00* (2006.01)
*H01J 37/26* (2006.01)

(52) U.S. Cl.
CPC .............. *H01J 37/20* (2013.01); *G01B 15/00* (2013.01); *H01J 37/26* (2013.01); *H01J 2237/221* (2013.01); *H01J 2237/24578* (2013.01)

(58) Field of Classification Search
CPC ........ H01J 37/26; H01J 37/28; H01J 2237/26; H01J 2237/2602; H01J 2237/282; H01J 2237/2826; H01J 2237/30433

USPC .... 250/305, 306, 307, 309, 310, 311, 492.1, 250/492.2, 492.21, 492.22, 492.23, 492.3
See application file for complete search history.

(56) References Cited

U.S. PATENT DOCUMENTS 5,604,819 A * 2/1997 Barnard .................... G06T 5/20
382/151

FOREIGN PATENT DOCUMENTS

JP    5243355 A    4/1977

* cited by examiner

*Primary Examiner* — Nicole Ippolito
(74) *Attorney, Agent, or Firm* — The Webb Law Firm

(57) ABSTRACT

There is provided a method capable of calibrating a sample stage easily. This method is for use in a charged particle beam system having the sample stage for moving a sample and an imaging subsystem for capturing a charged particle beam image and obtaining a final image. The method includes the steps of obtaining the final image from the imaging subsystem (step S100), obtaining correlation information that associates a given position in the final image with a position of the sample stage assumed when the final image was taken (step S102), obtaining length information about a length per pixel of the final image at a final magnification (step S106), and finding a correction between coordinates of the final image and coordinates of the sample stage on the basis of the correlation information and of the length information (step S110).

5 Claims, 5 Drawing Sheets

CALIBRATION METHOD AND CHARGED PARTICLE BEAM SYSTEM

CROSS-REFERENCE TO RELATED APPLICATION

This application and claims priority to Japanese Patent Application No. 2015-208771 filed Oct. 23, 2015, the disclosure of which is hereby incorporated in its entirety by reference.

BACKGROUND OF THE INVENTION

1. Field of the Invention

The present invention relates to a calibration method and a charged particle beam system.

2. Description of the Related Art

Electron microscopes such as transmission electron microscopes (TEMs) and scanning electron microscopes (SEMs) are currently in use in various fields to observe microstructural morphologies of samples.

It is known that one function of such an electron microscope is to automate movement of a sample stage into an arbitrary point on a resulting final image that can be directly viewed or recorded such as a TEM image or SEM image when the arbitrary point is specified on the final image.

For example, patent document 1 discloses a sample moving device for use in a charged particle beam system, the moving device being capable of improving the operability of the system by automating the movement of a sample during a search for a desired field of view. This moving device is equipped with a drive means for mechanically varying the position of a sample relative to a particle beam. The amount of motion of the moving means is controlled based on an electrical signal produced from a light detection means that detects an arbitrary position within the image of the sample displayed on an image display means.

One situation where the above-described function is used arises when high magnification imaging is done after obtaining a low-magnification final image that covers a whole TEM grid and moving into a desired position on the final image. Another situation where the above-described function is used occurs when plural portions are imaged at high magnification and a desired one of these imaged portions is again observed after returning to the location of this desired portion.

CITATION LIST

Patent Documents

Patent document 1: JP-A-52-43355

In order to implement the above-described function of automatically moving a sample stage into a specified position on a final image, the sample stage must be calibrated such that a correlation is previously provided between coordinates of the final image and coordinates of the sample stage.

SUMMARY OF THE INVENTION

One object associated with some aspects of the present invention is to provide a method capable of calibrating a sample stage easily. Another object associated with some aspects of the invention is to provide a charged particle beam system in which a sample stage can be calibrated easily.

(1) A method associated with the present invention is adapted to calibrate a sample stage in a charged particle beam system which has an imaging subsystem for capturing a charged particle beam image and obtaining a final image that can be directly viewed or recorded, as well as the sample stage for moving a sample. The method starts with obtaining the final image from the imaging subsystem. Then, there is obtained correlation information that associates a given position on the sample stage with a position of the sample stage at which the final image was obtained. Then, there is obtained length information about a length per pixel of the final image at a final magnification. A correlation between coordinates of the final image and coordinates of the sample stage is found based on the correlation information and on the length information.

In this calibration method, a correlation between the coordinates of the final image and the coordinates of the sample stage is found based on the correlation information and on the length information. Therefore, the sample stage can be easily calibrated using the final image. In consequence, in the charged particle beam system, the sample stage can be moved into a position specified on the final image.

(2) In one feature of this calibration method of (1) above, there may be further included the step of writing the correlation information and the length information into an image file of the final image.

(3) In another feature of the calibration method of (1) or (2), the charged particle beam system may have a controller for controlling the sample stage. The controller may perform the step of moving the sample stage into a position specified on the final image, based on the correlation between the coordinates of the final image and the coordinates of the sample stage.

(4) A charged particle beam system associated with the present invention has a sample stage for moving a sample, an imaging subsystem for capturing an image of a charged particle beam and obtaining a final image, and a controller for controlling the sample stage. The controller operates to obtain the final image from the imaging subsystem, to obtain correlation information that associates a given position in the final image with a position on the sample stage assumed when the final image was obtained, to obtain length information about a length per pixel of the final image at a final magnification, and to find a correlation between coordinates of the final image and coordinates of the sample stage on the basis of the correlation information and of the length information.

In this charged particle beam system, the controller operates to calibrate the sample stage by the use of the final image. Therefore, the sample stage can be calibrated easily using the final image. Consequently, in this charged particle beam system, the sample stage can be moved into a position specified on the final image.

(5) In one feature of this charged particle beam system of (4) above, the controller may operate to move the sample stage into a position specified on the final image on the basis of the correlation between the coordinates of the final image and the coordinates of the sample stage.

DETAILED DESCRIPTION OF THE INVENTION

The preferred embodiments of the present invention are hereinafter described in detail with reference to the drawings. It is to be understood that the embodiments described below are not intended to unduly restrict the content of the present invention delineated by the claims and that not all the configurations described below are essential constituent components of the invention.

1. Charged Particle Beam System

Figure 1:
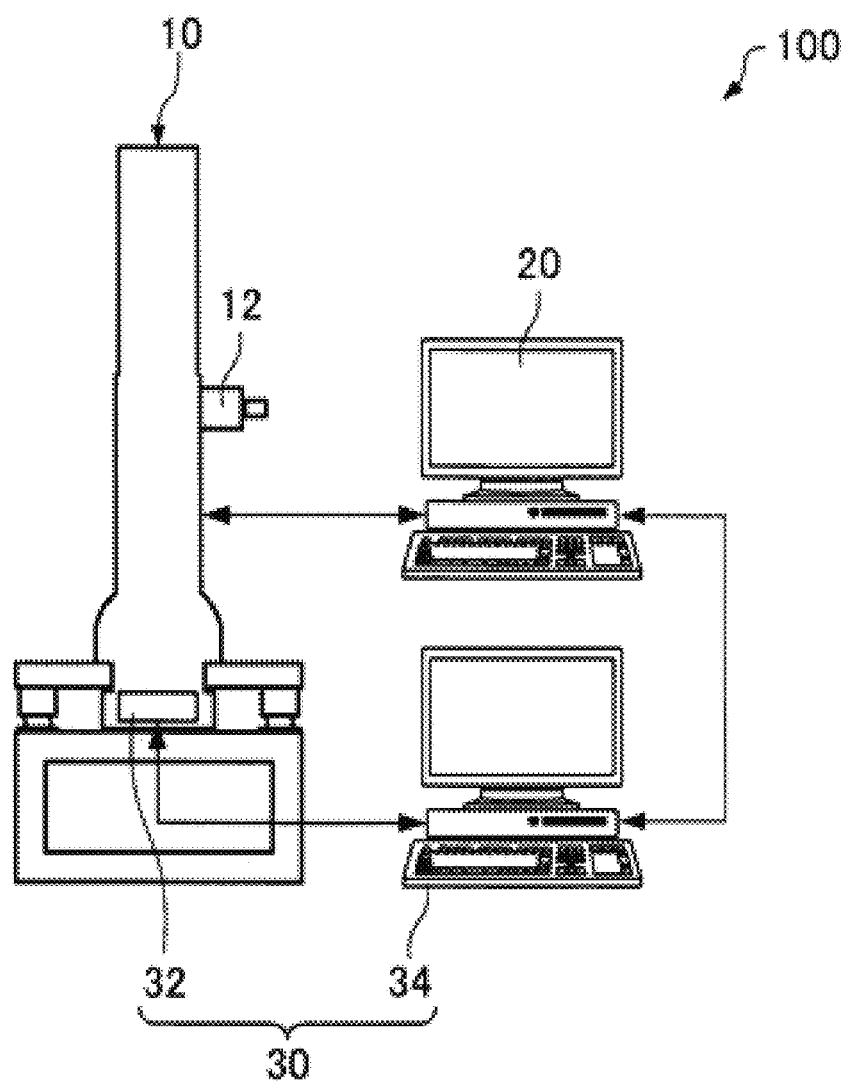
FIG. 1 is a schematic representation of a charged particle beam system associated with one embodiment of the present invention, showing the configuration of the system.

A charged particle beam system associated with one embodiment of the present invention is first described by referring to FIG. 1, which schematically shows the configuration of the charged particle beam system, generally indicated by reference numeral 100.

The charged particle beam system 100 is a transmission electron microscope (TEM), for example. Note that the charged particle beam system 100 is not restricted to transmission electron microscopes but rather may be any instrument which irradiates a sample with charged particles (such as electrons or ions) and which performs imaging. The charged particle beam system 100 may also be a scanning electron microscope (SEM), a scanning transmission electron microscope (STEM), a focused ion beam (FIB) system, or the like. An example is given below in which the charged particle beam system 100 is a transmission electron microscope.

As shown in FIG. 1, the charged particle beam system 100 whose body portion is indicated by numeral 10 includes a personal computer 20 for the operation of the body portion 10 of the charged particle beam system and an imaging subsystem 30. The personal computer 20, which may be hereinafter also referred to as the body control PC 20, is one example of a controller.

The body portion 10 of the charged particle beam system 100 is configured including a sample stage 12 that holds a sample. The sample stage 12 may hold the sample via a sample holder. The sample stage 12 can move the sample and place it in position.

The body portion 10 of the charged particle beam system 100 is configured further including an electron beam source for producing an electron beam, an illumination lens system for focusing the electron beam onto the sample, and an imaging lens system for forming a TEM image from electrons transmitted through the sample. A TEM image is one example of charged particle beam image.

The personal computer (PC) 20 for the operation of the body portion of the charged particle beam system controls the sample stage 12. Furthermore, the body control PC 20 controls the illumination lens system, imaging lens system, and so on. That is, the PC 20 controls the body portion 10 of the charged particle beam system. The body control PC 20 has a manual control unit. In response to a user's command given via the manual control unit, the body control PC 20 controls the body portion 10 of the charged particle beam system. The body control PC 20 and the body portion 10 of the charged particle beam system are interconnected by a communication cable or the like.

The body control PC 20 is configured including the manual control unit, a display unit, a storage section, and a processing section. The manual control unit derives a control signal responsive to a user's manipulation and sends the signal to the processing section. For example, the manual control unit is made of buttons, keys, a touch panel display, or the like. The display unit provides a display of images (such as final images) generated by the processing section. For instance, the display unit is an LCD, a CRT, or the like. The storage section operates as a working area for the processing section, and is made of a RAM or the like. The storage section stores computer programs, data, and related information, and the processing section performs various computational operations and control operations according to the programs stored in the storage section. The functions of the processing section can be implemented either by hardware such as various processors (e.g., a CPU or a DSP) or an ASIC (e.g., a gate array) or by software. As the processing section executes programs stored in the storage section, the body control PC 20 operates as a controller for controlling the body portion 10 (especially, the sample stage 12) of the charged particle beam system.

The imaging subsystem 30 captures the TEM image focused by the body portion 10 of the charged particle beam system and creates a final image that can be directly viewed or recorded. The imaging subsystem 30 is configured including a camera 32 and a personal computer (PC) 34 for the operation of the camera 32.

The camera 32 captures the TEM image focused by the imaging lens system of the body portion 10 of the charged particle beam system. The camera 32 is a digital camera such as a CCD camera or a CMOS camera.

The camera control PC 34 receives image data about the captured image output from the camera 32 and produces a final image. The camera control PC 34 stores the produced final image into the storage section of the PC 34 in TIFF (Tagged Image File Format) format. No restriction is imposed on the file format for storage of the final image. The camera control PC 34 and the camera 32 are interconnected by a communication cable or the like. Also, the camera control PC 34 and the body control PC 20 are interconnected by a communication cable or the like.

The camera control PC 34 is configured including a manual control unit, a display unit, a storage section, and a processing section, in the same way as the body control PC 20.

2. Calibration Method

A method of calibrating the sample stage 12 in the charged particle beam system 100 is next described. This calibration of the sample stage 12 in the system 100 is performed using the final image. In particular, a correlation between coordinates of the sample stage 12 and coordinates of the final image is provided, and the coordinates of the sample stage 12 are made to correspond to the coordinates of the final image. The sample stage 12 can be moved into a position specified on the final image by calibrating the sample stage 12 using the final image.

The coordinates of the final image are used to identify pixels that make up the final image. The coordinates of the sample stage 12 are used to identify the position of the sample stage 12, and are two-dimensional coordinates, for example, within a horizontal plane perpendicular to the direction along which an electron beam is directed at the sample.

Figure 2:
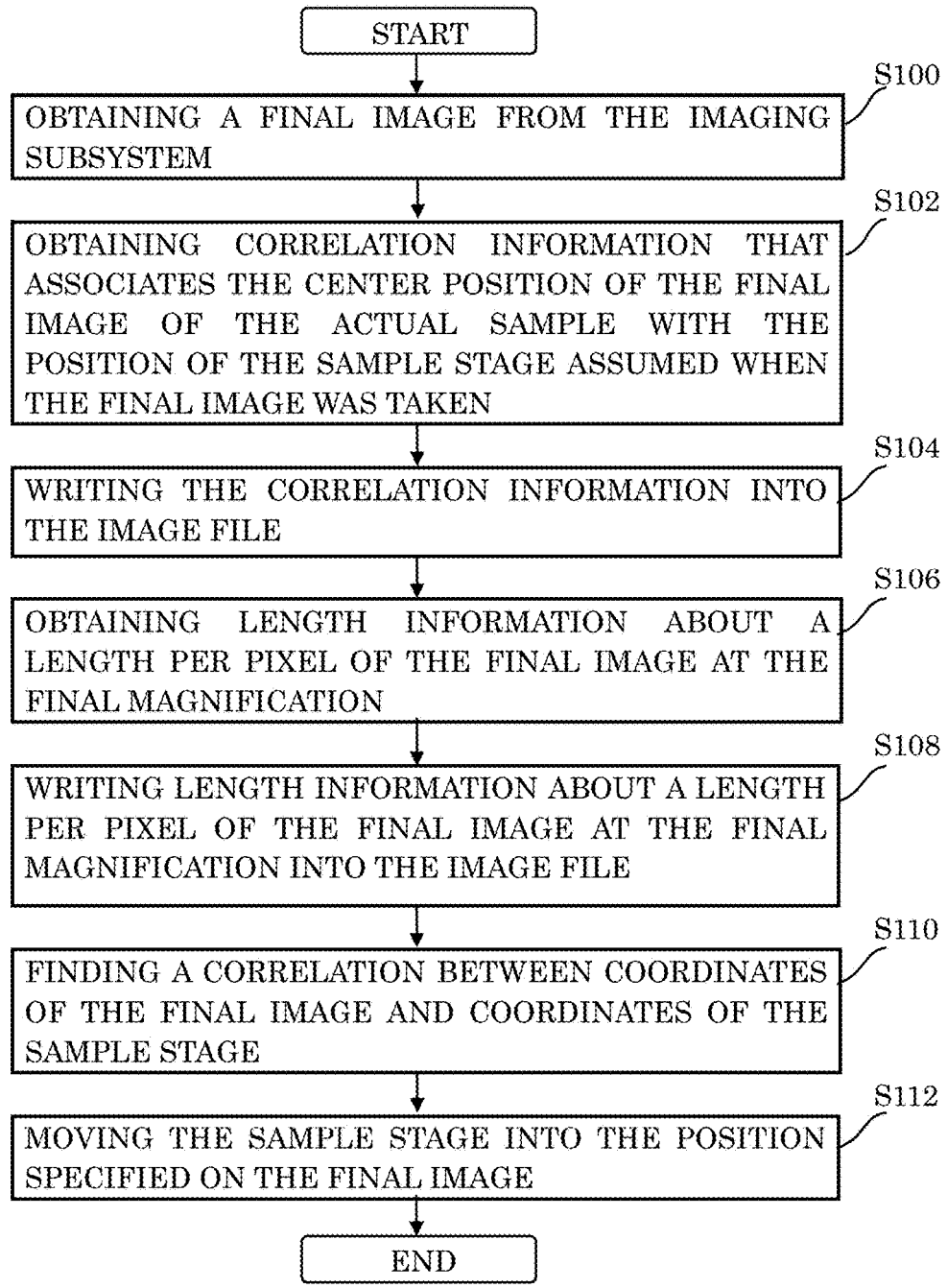
FIG. 2 is a flowchart illustrating one example of the calibration method associated with another embodiment of the invention.

FIG. 2 is a flowchart illustrating one example of calibration method associated with the present embodiment. First, the body control PC 20 obtains a final image from the imaging subsystem 30 (step S100).

The imaging subsystem 30 can capture the final image by permitting the TEM image of the sample focused by the body portion 10 of the charged particle beam system to be taken with the imaging subsystem 30. In the present step, shooting is done, for example, at such a low magnification that a part or a whole of a TEM grid is contained within the field of view, and a final image is acquired. The camera control PC 34 stores the acquired final image in TIFF format into the storage section of the PC 34.

If a user asks for initiation of a calibration via the manual control unit of the body control PC 20, the PC 20 sends a command to the camera control PC 34 to cause it to output a copy of a TIFF file of the final image acquired by the imaging subsystem 30. The camera control PC 34 accepts the command and outputs the TIFF file of the final image. The TIFF file of the image is then transferred to the body control PC 20. In this way, the body control PC 20 acquires the final image from the imaging subsystem 30. The body control PC 20 displays the final image on the display unit of the body control PC 20 based on the acquired TIFF file of the final image.

Then, the body control PC 20 obtains correlation information that associates the center position of the final image with the position of the sample stage 12 assumed when the final image was taken (step S102).

On receiving the TIFF file of the final image, the body control PC 20 associates the center position of the final image with the position of the sample stage 12 assumed when the final image was taken. That is, the position (coordinates) of the sample stage 12 assumed when the final image was captured is taken as the center position of the final image. If the sample stage 12 has not been moved after the capture of the final image, the body control PC 20 takes the present position (coordinates) of the sample stage 12 as the central position of the final image. Information that associates the center position of the final image with the position of the sample stage 12 assumed when the final image was taken is information about coordinates of the sample stage 12 which correspond, for example, to the center position of the final image.

It is herein assumed that the correlation information associates the center position of the final image with the position of the sample stage 12 assumed when the final image was taken. Alternatively, the correlation information may associate an arbitrary position or given position in the final image other than the center position of the final image with the position of the sample stage 12 assumed when the final image was taken.

Then, the body control PC 20 writes the obtained correlation information into the TIFF file of the final image (step S104).

The body control PC 20 writes the correlation information, for example, into the tag of the TIFF file of the final image. Consequently, the correlation information is appended to the TIFF file of the final image in addition to the image data.

Then, the body control PC 20 obtains length information about a length per pixel of the final image at the final magnification from the camera control PC 34 (step S106).

The length information about a length per pixel of the final image at the final magnification indicates a length (one side) of one pixel of the final image at the final magnification. The body control PC 20 obtains the length information about a length per pixel of the final image at the final magnification by deriving pixel size information about the camera 32 and final image information from the camera control PC 34.

The pixel size information about the camera 32 is information about the actual size of one pixel of the camera 32, i.e., the length of one side of one actual pixel. The final magnification information is information about the magnification of the final image to be taken, and is determined taking account both of the magnification of the body portion 10 of the charged particle beam system and of the magnification of the camera 32. That is, final magnification information is information about the ratio of the size of the sample image portion in a final image to the actual size of the sample. Length information about a length per pixel of the final image at the final magnification can be obtained from the pixel size information about the camera 32 and from the final magnification information.

As noted above, the length information about a length per pixel of the final image at the final magnification obtained by the body control PC 20 does not need to be this length information itself. That is, this information may be composed of plural sets of information that allow for acquisition of information about a length per pixel of the final image at the final magnification.

The body control PC 20 sends a command to the camera control PC 34 to cause it to output pixel size information and final image magnification information, for example. In response to the command, the camera control PC 34 outputs the pixel size information and final magnification information which are transferred to the body control PC 20. Thus, the body control PC 20 obtains the length information about a length per pixel of the final image at the final magnification.

Then, the body control PC 20 writes the obtained pixel size information and final magnification information into a TIFF file of the final image (step S108).

The body control PC 20 writes the pixel size information and final magnification information, for example, into the tag of the TIFF file of the final image. Consequently, the pixel size information and final magnification information (information about the length per pixel of the final image at the final magnification) are appended to the TIFF file of the final image, in addition to image data.

The body control PC 20 then finds a correlation between the coordinates of the final image and the coordinates of the sample stage 12, based on the correlation information and on the length information about a length per pixel of the final image at the final magnification (step S110). This means that at least some of the coordinates of pixels making up the final image are made to correspond to the coordinates of the sample stage 12.

The body control PC 20 reads the correlation information and the length information about a length per pixel of the final image at the final magnification (pixel size information and final magnification information) from the tag of the TIFF file of the final image and finds a correlation between the coordinates of the final image and the coordinates of the sample stage 12. The body control PC 20 can make the coordinates of all the pixels making up the final image correspond to their respective coordinates of the sample stage 12, based on the correlation information and on the length information about a length per pixel of the final image at the final magnification.

Then, the body control PC 20 moves the sample stage 12 into a position specified on the final image, based on the correlation between the coordinates of the final image and the coordinates of the sample stage (step S112).

Figure 3:
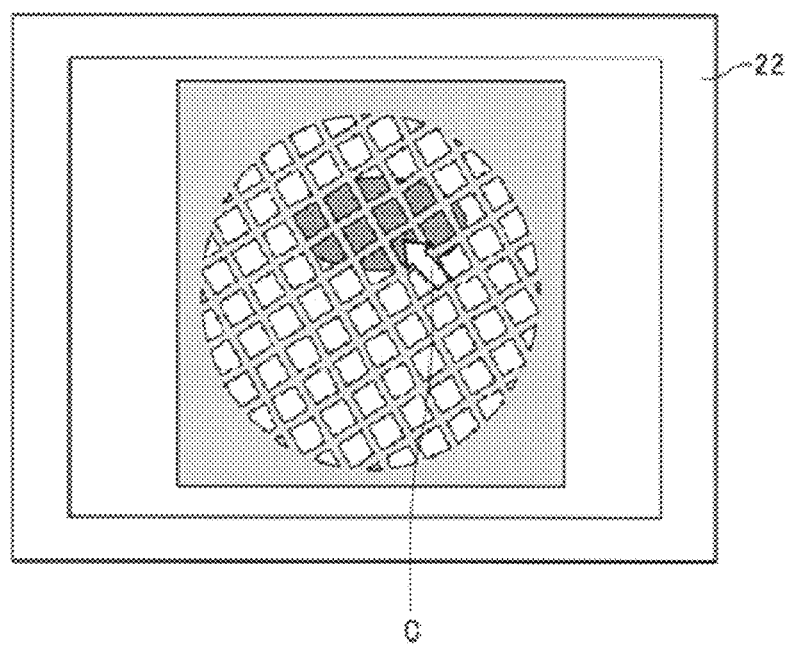
FIG. 3 is a schematic representation illustrating the manner in which a position is specified on a final image.

FIG. 3 illustrates how a position is specified on the final image that is displayed on the display unit 22 of the body control PC 20. As shown in FIG. 3, if the position is specified by manipulating a cursor C on the final image displayed on the display unit 22 with the manual control unit, the body control PC 20 converts the position specified on the final image into coordinates of the sample stage 12 based on the correlation between the coordinates of the final image and the coordinates of the sample stage 12. The processing section of the body control PC 20 provides control to move the sample stage 12 into the resulting coordinates. As a result, the sample stage 12 moves into the position specified on the final image. That is, the sample stage 12 moves in such a way that the position specified on the final image is located in the center of the field of view. Because of the processing steps described so far, the body control PC 20 ends the present processing subroutine.

The calibration method associated with the present embodiment has the following features. The calibration method includes obtaining a final image from the imaging subsystem 30 (step S100), obtaining correlation information that associates a center position or a given position in the final image with the position of the sample stage 12 assumed when the final image was taken (step S102), obtaining length information about a length per pixel of the final image at the final magnification (step S106), and finding a correlation between coordinates of the final image and coordinates of the sample stage 12 on the basis both of the correlation information and of the length information about a length per pixel of the final image at the final magnification (step S110).

In this calibration method, a correlation between the coordinates of the final image and the coordinates of the sample stage 12 is found based on the correlation information and on the length information about a length per pixel of the final image at the final magnification. Therefore, the sample stage 12 can be easily calibrated using the final image and so in the charged particle beam system 100, the sample stage 12 can be moved into the position specified on the final image. Consequently, in the charged particle beam system 100, it is possible that a low-magnification final image is first obtained and then a high-magnification final image can be obtained after moving into a desired position on the low-magnification final image. Where high-magnification imaging is done at plural locations, an observation can be performed again at a desired one of these locations after returning to this desired location.

Furthermore, in the calibration method associated with the present embodiment, if the body control PC 20 and the imaging subsystem 30 are available from different manufacturers, for example, and thus the PC 20 and the imaging subsystem 30 have no compatibility, the sample stage 12 can be calibrated using a final image.

The charged particle beam system 100 has the following features. In the charged particle beam system 100, the body control PC 20 that acts as a controller performs the steps of obtaining a final image from the imaging subsystem 30, obtaining correlation information that associates a center position or a given position in the final image with the position of the sample stage 12 assumed when the final image was taken, obtaining length information about a length per pixel of the final image at the final magnification, and finding a correlation between coordinates of the final image and coordinates of the sample stage 12 on the basis both of the correlation information and of the length information about a length per pixel of the final image at the final magnification.

In this way, in the charged particle beam system 100, the body control PC 20 performs processing to calibrate the sample stage 12 using the final image and so the sample stage 12 can be easily calibrated using the final image. Consequently, in the charged particle beam system 100, the sample stage 12 can be moved into a position specified on the final image.

In the charged particle beam system 100, the body control PC 20 performs processing to move the sample stage 12 into a position specified on the final image on the basis of a correlation between coordinates of the final image and coordinates of the sample stage. Consequently, in the charged particle beam system 100, it is possible that low-magnification imaging is done and then high-magnification imaging is effected after moving into a desired position on the low-magnification final image. Furthermore, where high-magnification imaging is done at plural locations, an observation can be performed again at a desired one of these locations after returning to this desired location.

3. Modifications 3.1. First Modification

A first modification of the calibration method associated with the present embodiment is next described. Only the differences with the above-described calibration method associated with the present embodiment are described; a description of similarities is omitted here.

The calibration method associated with the first modification is different from the above-described calibration method associated with the present embodiment in step (step S106) of obtaining length information about a length per pixel of the final image at the final magnification.

In particular, in the above embodiment, the body control PC 20 sends a command to the camera control PC 34 to cause it to output pixel size information and final magnification information, and obtains the pixel size information and final magnification information transferred from the camera control PC 34.

On the other hand, in the calibration method associated with the first modification, the body control PC 20 accepts the pixel size information and the final magnification information input via the manual control unit and obtains these two kinds of information.

The user performs manipulations to read the pixel size information and the final magnification information, for example, from the camera control PC 34 and confirms these kinds of information. The pixel size information may be checked against a specification, catalog, or the like for the imaging subsystem 30. The user enters the pixel size information and the final magnification information into the body control PC 20 via the manual control unit. Consequently, the body control PC 20 can obtain the pixel size information and the final size information (length information about a length per pixel of the final image at the final magnification). The user may write these kinds of information into the tag of the TIFF file of the final image through the manual control unit.

The calibration method associated with the first modification can produce advantageous effects similar to those provided by the calibration method associated with the present embodiment.

3.2. Second Modification

Figure 4:
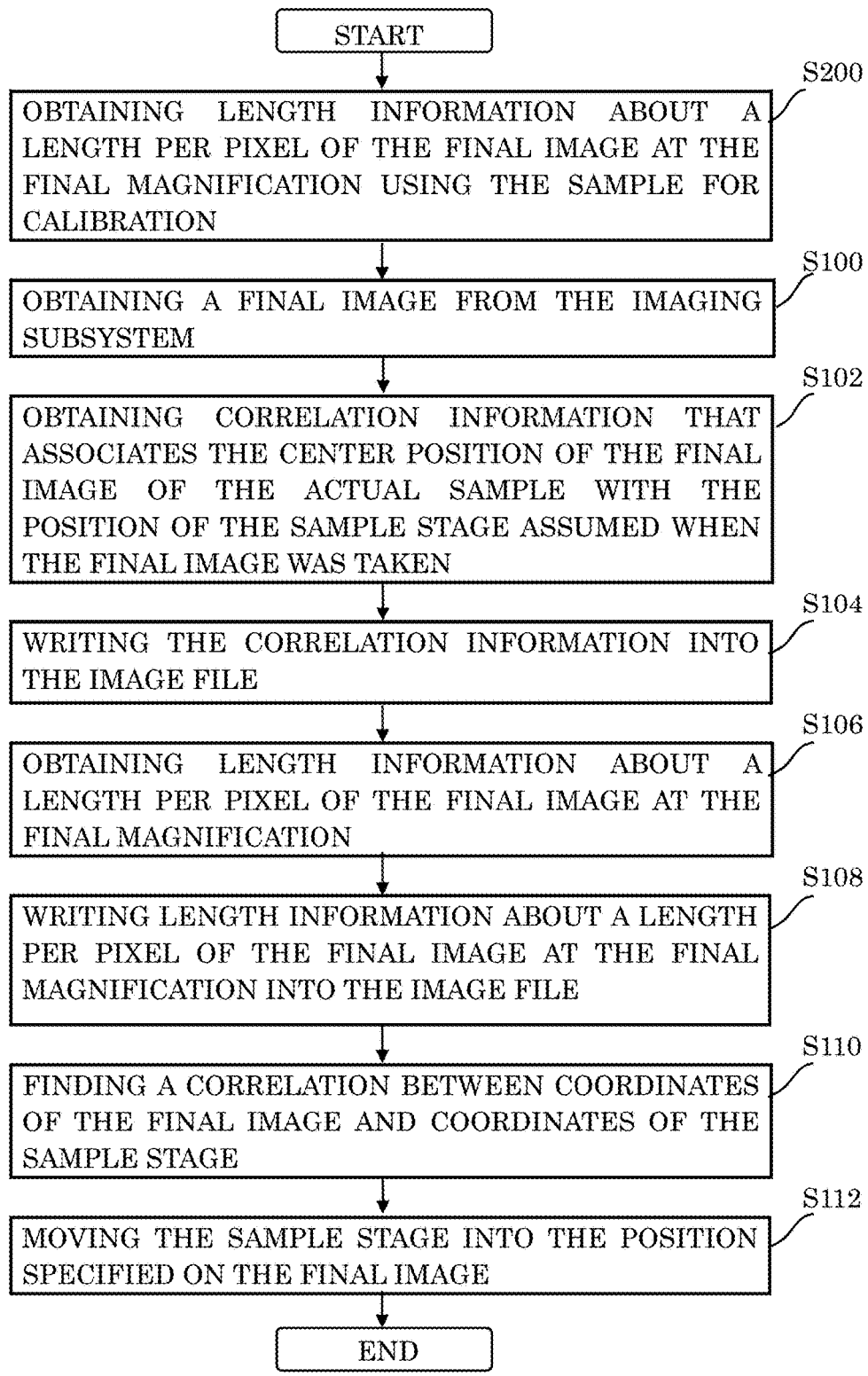
FIG. 4 is a flowchart illustrating one example of the calibration method associated with a second modification.

A second modification of the calibration method associated with the present embodiment is next described by referring to FIG. 4, which is a flowchart illustrating one example of the calibration method associated with the second modification.

The calibration method associated with the second modification is different from the calibration method associated with the present modification and illustrated in FIG. 2 in terms of step (step S200) of obtaining length information about a length per pixel of the final image at the final magnification using a sample (i.e., a sample for calibration) having a known length, as illustrated in FIG. 4.

The calibration method associated with the second modification starts with obtaining length information about a length per pixel of the final image at the final magnification using the sample for calibration (step S200).

In particular, a TEM image of a sample for calibration is first focused by the body portion 10 of the charged particle beam system. The TEM image is captured by the imaging subsystem 30. Thus, the imaging subsystem 30 obtains the final image for calibration. Examples of the sample for calibration are a grating, one side of a hole in a square mesh grid, a hole in a film of Quantifoil (trademark), or the like. The final image for calibration is an image containing a portion or portions having such a known length.

The body control PC 20 sends a command to the camera control PC 34 to cause it to output a copy of the TIFF file of the final image for calibration, the final image being captured by the imaging subsystem 30, and obtains the final image for calibration. The body control PC 20 displays the final image for calibration on the display unit, based on the TIFF file of the obtained final image for calibration.

Then, the length of the portion of the known length in the final image for calibration is measured, the final image being displayed on the display unit of the body control PC 20.

Figure 5:
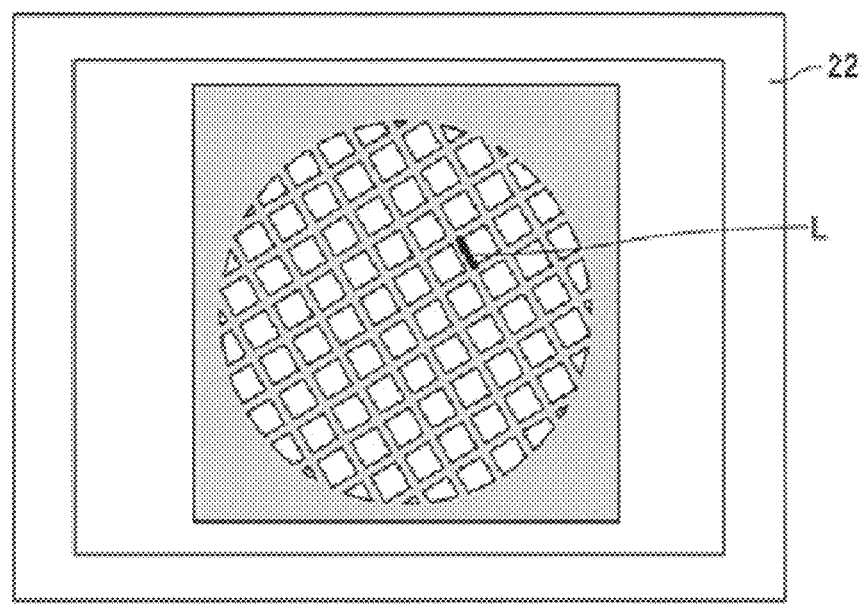
FIG. 5 is a schematic representation illustrating the manner in which a portion with a known length is measured in terms of length, the portion being a part of an image to be taken for calibration.

FIG. 5 schematically shows the manner in which the portion of the known length is measured, the portion being in the final image for calibration.

A length measurement of the portion of the known length is carried out, as shown in FIG. 5, by drawing a line L on the portion of the known length within the final image for calibration displayed on the display unit 22 with the manual control unit (such as a mouse) of the body control PC 20 and measuring the length of the line L. The user enters the result of the measurement (information about the length of the line L), information about the current magnification, and other related data into the processing section through the manual control unit. The processing section of the body control PC 20 calculates the length per pixel of the final image at the final magnification, based on the entered information. Consequently, information about the length per pixel of the final image at the final magnification can be obtained.

Then, the sample for calibration is taken from the sample stage 12 and an actual sample that is an actual subject of observation is loaded onto the sample stage 12 of the body portion 10 of the charged particle beam system.

The body control PC 20 then obtains the final image from the imaging subsystem 30 (step S100). A final image of an actual sample can be obtained by the imaging subsystem 30 by making the imaging system 30 capture a TEM image of the actual sample focused by the body portion 10 of the charged particle beam system. Preferably, the final magnification of the actual sample is the same as the condition under which an image of the sample for calibration is captured. This can enhance the accuracy with which the sample stage 12 is moved into the position specified on the final image. The final magnification of the actual sample may be different from the final magnification of the sample for calibration.

The body control PC 20 then obtains correlation information that associates the center position of the final image of the actual sample with the position of the sample stage 12 assumed when the final image was taken (step S102).

The body control PC 20 then writes the obtained correlation information into the TIFF file of the final image (step S104).

The body control PC 20 then obtains length information about a length per pixel of the final image at the final magnification (step S106).

In the present step, with respect to the length information (computed at step S200) about a length per pixel of a final image at the final magnification obtained using the final image for calibration, the body control PC 20 obtains this length information as length information about a length per pixel of a final image of the actual sample at the final magnification. The user may enter the length information (computed at step S200) about a length per pixel of the final image at the final magnification into the body control PC 20 via the manual control unit, the length being determined using the final image for calibration.

Then, the body control PC 20 writes the obtained length information about a length per pixel of the final image at the final magnification into the TIFF file of the final image (step S108).

The body control PC 20 then finds a correlation between coordinates of the final image and coordinates of the sample stage 12 on the basis both of the correlation information and of the length information about a length per pixel of the final image at the final magnification (step S110).

The body control PC 20 then moves the sample stage 12 into the position specified on the final image, based on the correlation between the coordinates of the final image and the coordinates of the sample stage (step S112).

The calibration method associated with the second modification can yield advantageous effects similar to those provided by the calibration method associated with the present embodiment. Furthermore, in the calibration method associated with the second modification, if length information about a length per pixel of the final image at the final magnification is not obtained from the camera control PC 34, the sample stage 12 can be calibrated.

In the second modification, the sample for calibration and the actual sample are separate samples. The sample for calibration and the actual sample may also be the same. For example, the sample for calibration and the actual sample can be made identical by using as a TEM grid for supporting the subject of observation a square mesh grid in which the length of one side of each hole is known. In this case, in the body portion 10 of the charged particle beam system, it is possible to eliminate the labor in exchanging the sample for calibration and the actual sample.

It is to be understood that the above-described embodiments and modifications are merely exemplary and that the invention is not restricted thereto. For example, the embodiments and modifications may be appropriately combined.

The present invention embraces configurations substantially identical (e.g., in function, method, and results or in purpose and advantageous effects) with the configurations described in any one of the embodiments of the invention. Furthermore, the invention embraces configurations described in the embodiments and including portions which have non-essential portions replaced. In addition, the invention embraces configurations which produce the same advantageous effects as those produced by the configurations described in the embodiments or which can achieve the same objects as the configurations described in the embodiments. Further, the invention embraces configurations which are similar to the configurations described in the embodiments except that well-known techniques have been added.

What is claimed is:

1. A method of calibrating a sample stage in a charged particle beam system having an imaging subsystem for capturing a charged particle beam image and obtaining a final image that can be directly viewed on a display having a given pixel size or recorded as well as the sample stage for moving a sample, said method comprising the steps of:

obtaining the final image from the imaging subsystem;

obtaining correlation information that associates a given position in the final image with a position of the sample stage as defined by the two-dimensional coordinates of the sample stage assumed when the final image was obtained;

obtaining length information about a length per pixel of the final image at a final magnification; and finding a correlation between pixel coordinates of the final image and two-dimensional coordinates of the sample stage defining a position of the sample stage on the basis of the correlation information and of the length information.

2. A calibration method as set forth in claim 1, further comprising the step of writing said correlation information and said length information into an image file of said final image.

3. A calibration method as set forth in claim 1, wherein said charged particle beam system has a controller for controlling said sample stage, and wherein the controller performs the step of moving the sample stage into a position specified on the final image on the basis of the correlation between the coordinates of the final image and the coordinates of the sample stage, and wherein when a position is specified on the final image displayed on a display, the controller performs the steps of converting the position specified on the final image into coordinates of the sample stage based on the correlation and moving the sample stage into a position defined by the coordinates of the sample stage obtained by the step of conversion.

4. A charged particle beam system comprising:

a sample stage for moving a sample;

an imaging subsystem for capturing a charged particle beam image and obtaining a final image; and a controller for controlling the sample stage;

wherein the controller operates to obtain the final image from the imaging subsystem, to obtain correlation information that associates a given position in the final image with a position of the sample stage assumed when the final image was obtained, to obtain length information about a length per pixel of the final image at a final magnification, and to find a correlation between pixel coordinates of the final image and two-dimensional coordinates of the sample stage defining a position on the sample stage on the basis of the correlation information and of the length information.

5. A charged particle beam system of claim 4, wherein said controller further comprises a display for displaying the final image and a pointing device capable of pointing a position on the final image displayed on the display, and said controller performs the step of converting the position specified on the final image into coordinates of the sample stage and operates to move the sample stage into a position specified on said final image on the basis of the correlation between the pixel coordinates of the final image and the two-dimensional coordinates of the sample stage.

* * * * *